United States Patent
Song et al.

(10) Patent No.: US 9,839,601 B2
(45) Date of Patent: Dec. 12, 2017

(54) METHOD OF FRIZZ REDUCTION USING A COMPOSITION COMPRISING A CROSSLINKABLE SILICONE

(71) Applicant: The Procter & Gamble Company, Cincinnati, OH (US)

(72) Inventors: Brian Xiaoqing Song, Mason, OH (US); Tiffany Tien-Yun Yang, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 18 days.

(21) Appl. No.: 14/751,622

(22) Filed: Jun. 26, 2015

(65) Prior Publication Data

US 2016/0374932 A1  Dec. 29, 2016

Related U.S. Application Data

(60) Provisional application No. 62/018,161, filed on Jun. 27, 2014.

(51) Int. Cl.

| | |
|---|---|
| *A61K 8/02* | (2006.01) |
| *A61K 8/898* | (2006.01) |
| *A61Q 5/12* | (2006.01) |
| *A61K 8/92* | (2006.01) |
| *A61K 8/891* | (2006.01) |
| *A61Q 5/02* | (2006.01) |
| *A61Q 5/06* | (2006.01) |
| *A61K 8/06* | (2006.01) |

(52) U.S. Cl.
CPC .............. *A61K 8/898* (2013.01); *A61K 8/062* (2013.01); *A61K 8/891* (2013.01); *A61K 8/922* (2013.01); *A61Q 5/02* (2013.01); *A61Q 5/06* (2013.01); *A61Q 5/12* (2013.01); *A61K 2800/21* (2013.01); *A61K 2800/592* (2013.01)

(58) Field of Classification Search
CPC . A61K 8/737; A61K 8/44; A61K 8/92; A61K 2800/87; A61K 8/06; A61K 8/34; A61K 8/442; A61K 8/463; A61K 8/894; A61K 2800/20; A61K 8/23; A61K 8/345; A61K 8/49; A61Q 5/12; A61Q 5/02; A61Q 5/004; A61Q 5/10; A61Q 5/00; A61Q 5/002; A61Q 5/5066; A61Q 5/06; A61Q 5/65; A61Q 13/00
See application file for complete search history.

(56) References Cited

U.S. PATENT DOCUMENTS

| | | | |
|---|---|---|---|
| 8,900,329 B2 | 12/2014 | Schulze zur Wiesche et al. | |
| 8,900,561 B2 | 12/2014 | Schulze zur Wiesche | |
| 8,999,310 B1 * | 4/2015 | Frank .................. | A61K 8/895 |
| | | | 132/206 |
| 9,066,892 B2 | 6/2015 | Schulze zur Wiesche | |
| 9,421,160 B2 | 8/2016 | Schulze zur Wiesche et al. | |
| 2003/0113391 A1 * | 6/2003 | Brown .................. | A61K 8/23 |
| | | | 424/769 |
| 2007/0286837 A1 | 12/2007 | Torgerson et al. | |
| 2008/0064813 A1 | 3/2008 | Schneider | |
| 2014/0116458 A1 | 5/2014 | Krueger | |
| 2014/0161756 A1 | 6/2014 | Beer et al. | |
| 2015/0101631 A1 | 4/2015 | Schulze Zur Wiesche et al. | |

FOREIGN PATENT DOCUMENTS

| | | |
|---|---|---|
| EP | 2749322 A1 | 7/2014 |
| EP | 2687265 B1 | 11/2015 |

OTHER PUBLICATIONS

PCT International Search Report and Written Opinion for PCT/US2015/037944 dated Aug. 12, 2015.

\* cited by examiner

*Primary Examiner* — Nannette Holloman
(74) *Attorney, Agent, or Firm* — Linda M. Sivik (57) ABSTRACT

The present invention is directed to a method of reduction of frizz and improving hair conditioning wherein a hair treatment composition comprising a silicone emulsion with droplets having an average diameter of less than about 50 nanometers in an carrier wherein the silicone emulsion comprises a crosslinked organopolysiloxane made from various reactive compounds, wherein each compound is comprised of one or more units represented by the following general formula:

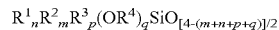

where
$R^1$ is morpholinomethyl having the structure:

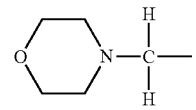

$R^2$ is
—$(CH_2)_3$—NH—$(CH_2)_2NH_2$
—$(CH_2)_3$—$NH_2$
$R^3$ is methyl
$R^4$ is hydrogen, methyl, ethyl or propyl
n is 0, 1, or 2
m is 0, 1, or 2
p is 0, 1, or 2
q is 0, 1, 2 or 3
n+m+p+q is less than or equal to 3
and wherein the crosslinked organopolysiloxane comprises on average at least one radical $R^1$ per molecule and
wherein the method comprises the following steps:
  a) applying the hair treatment composition to hair by spraying or spreading;
  b) allowing hair to dry by air or heat.

14 Claims, 2 Drawing Sheets

METHOD OF FRIZZ REDUCTION USING A COMPOSITION COMPRISING A CROSSLINKABLE SILICONE

FIELD OF THE INVENTION

The present invention relates to a method of reduction of frizz on hair using a composition comprising a durable silicone.

BACKGROUND OF THE INVENTION

Frizzy hair is one of the main problems that many consumers deal with on a daily basis. It is unruly hair after the loss of sleekness and smoothness. It is seen as unruly hair fibers sticking out, curling and bending out at the top of the head and from the bulk of hair to different directions as well as an increased volume through the bulk of the hair. Generally consumers experience frizz on humid days when the level of moisture in the air is high. Frizz is undesirable, messy and is often associated with the loss of shine and smoothness as well as with the perception of poor hair health. The basic mechanism causing frizz in high humid environments is that at high humidity moisture penetrates into hair and changes the intermolecular interactions between proteins inside the hair fibers. During styling, the consumer will create a 'wet set' where hair is blow dried or flat ironed to create the desired shape. During drying, water is evaporated from hair and hydrogen bonds are formed between the protein peptide chains holding the style in place. As moisture from the environment diffuses into hair the hydrogen bonds are broken and hair returns back to its natural shape. For consumers with curly hair who straighten their hair by blow drying or flat ironing this return to a curled style is associated with a loss of alignment and increased volume. In addition, at high moisture levels in hair the fiber diameter increases which also increases the overall volume of hair.

The typical strategy to prevent frizz is to formulate leave-on products with surface-depositing materials such as silicone, oils, conditioning materials etc. which make hair more hydrophobic and decrease inter-fiber interactions. At high levels these materials can also provide increased cohesive forces holding fibers together to prevent frizz from occurring. However in order to provide some frizz control benefits, high levels of these materials are required which typically make the hair look greasy or weigh down. If used at lower levels that don't cause the greasy or weigh down negatives (as the fibers don't have enough materials on the surface form cohesive bonds), they are not effective controlling frizz.

The present invention has unexpectedly found certain film forming silicone materials, when applied at levels not causing greasy or weigh down negatives, delivers breakthrough frizz control benefits compared to other non-film forming silicone materials. Without being bound by theory, these film forming materials work by changing the balance of the mechanic forces of hair fiber which lead to an overall force equal or greater than the internal force of hair fiber returning to its natural curl after straightening or styling (i.e., wet set). In other words, the thin film evenly distributed on the hair fiber surface increases hair fiber bending and torsional modulus that overcomes the natural internal force of returning to natural shape). In addition, these film forming silicones resist from being removed by washing, therefore delivering longer lasting frizz control and other conditioning benefits. Consequently, a need exists for a treatment product that combines effective long lasting frizz control with silky and softness benefits typically offered by silicones without being greasy and weight down, and without the crunch coated feeling caused by using styling gel or styling polymers.

SUMMARY OF THE INVENTION

The present invention is directed to a method of reduction of frizz and improving hair conditioning wherein a hair treatment composition comprising a silicone emulsion with droplets having an average diameter of less than 50 nanometers in an carrier wherein the silicone emulsion comprises a crosslinked organopolysiloxane made from various reactive compounds, wherein each compound is comprised of one or more units represented by the following general formula:

where
$R^1$ is morpholinomethyl having a structure:

$R^2$ is
—$(CH_2)_3$—NH—$(CH_2)_2NH_2$ or —$(CH_2)_3$—$NH_2$
$R^3$ is methyl
$R^4$ is hydrogen, methyl, ethyl or propyl
n is 0, 1, or 2
m is 0, 1, or 2
p is 0, 1, or 2
q is 0, 1, 2 or 3
n+m+p+q is less than or equal to 3
and wherein the crosslinked organopolysiloxane comprises on average at least one radical $R^1$ per molecule and wherein the method comprises the following steps:
a) applying the hair treatment composition to hair by spraying or spreading;
b) allowing hair to dry by air or heat.

DETAILED DESCRIPTION OF THE INVENTION

In all embodiments of the present invention, all percentages are by weight of the total composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

The term "comprising," as used herein, means that other steps and other ingredients which do not affect the end result can be added. This term encompasses the terms "consisting of" and "consisting essentially of." The compositions and methods/processes of the present invention can comprise, consist of, and consist essentially of the elements and limitations of the invention described herein, as well as any of the additional or optional ingredients, components, steps, or limitations described herein.

The terms "include," "includes," and "including," as used herein, are meant to be nonlimiting and are understood to mean "comprise," "comprises," and "comprising," respectively. The test methods disclosed in the Test Methods Section of the present application should be used to determine the respective values of the parameters of Applicants' inventions.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated. The term "weight percent" may be denoted as "wt. %" herein.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The chemical nature of the monomers used for the making of the siloxanes polymer influences the structure of the resulting polymer. More specifically, the monomeric silane units may contain, in addition to 1, 2, or 3 organic groups that are connected to the silicone atom via Silicone-Carbon bond, 4, 3, 2 or 1 reactive groups attached to the silicone atom, such as chloride or alkoxy group.

In order to identify the nomenclature of silicone corresponding structures, the industry uses an abbreviated nomenclature to describe building blocks of structures such as M, D, T, and Q, as indicated below.

Silicones

"M unit" is monosubstituted (one oxygen atom on silicon). End of chain.

"D unit" is disubstituted (two oxygen atoms on silicon). Straight Chain

"T unit" is trisubstituted (three oxygen atoms on silicon). Branched or Cyclic

"Q unit" is tetrasubstituted (four oxygen atoms on silicon) Three dimensional structure/caged structure.

Some non-limiting examples are provided below:
a. $MD_nM$ corresponds to the structure: $Me_3SiO(SiMe_2O)_nSiMe_3$
b. $D_5$ corresponds to the cyclic structure decamethylpentacyclosiloxane $(SiMe_2O)_4$ The use of mixtures of monomeric materials and the fact that these may be partially hydrolyzed, results in the final siloxane polymer that contains a variety of structural features such as linear, branched, crosslinked, and caged portions.

In an embodiment of the present invention an aqueous composition may comprise at least one conditioning agent of crosslinked organopolysiloxanes made from various reactive compounds, wherein each compound is comprised of one or more units represented by the following general formula:

$$R^1_n R^2_m R^3_p (OR^4)_q SiO_{[4-(m+n+p+q)]/2}$$

where
$R^1$ is morpholinomethyl having a structure:

$R^2$ is
$-(CH_2)_3-NH-(CH_2)_2NH_2$ or $-(CH_2)_3-NH_2$
$R^3$ is methyl
$R^4$ is hydrogen, methyl, ethyl or propyl
n is 0, 1, or 2
m is 0, 1, or 2
p is 0, 1, or 2
q is 0, 1, 2 or 3 n+m+p+q is less than or equal to 3 and wherein the crosslinked organopolysiloxane comprises on average at least one radical $R^1$ per molecule.

In an embodiment of the present invention, the crosslinked organopolysiloxane used in the present invention have a particle size of less than about 50 nanometers. In a further embodiment, the crosslinked organopolysiloxane used in the present invention have a particle size of less than about 60 nanometers, in a further embodiment the crosslinked organopolysiloxane used in the present invention have a particle size of less than about 70 nanometers. Particle size may be measured by means of a laser light scattering technique, using a Horiba model LA-930 Laser Scattering Particle Size Distribution Analyzer (Horiba Instruments, Inc.). In another embodiment of the present invention, the crosslinked organopolysiloxane used in the present invention may form elastomeric films after removing the water.

Non-limiting examples of a crosslinked organopolysiloxane include Belsil ADM 8301 E: INCI Amodimethicone/ Morpholinomethyl/Silsesquioxane Copolymer, Trideceth-5, Glycerin Emulsion contains 20% active materials; pH approx. 6; Nonionic microemulsion of aminofunctional polydimethysiloxane; and Belsil ADM 6300E: INCI Amodimethicone/Morpholinomethyl/Silsesquioxane Copolymer, Trideceth-5. Emulsion contains 35% active materials, pH approx. 5.5, Nonionic microemulsion of aminofunctional polydimethysiloxane.

In a further embodiment of the present invention, a crosslinked organopolysiloxane may be used in a method wherein the method comprises the following steps: a) applying the hair treatment composition to hair by spraying or spreading; and b) allowing hair to dry by air or heat.

In a further embodiment, the method may comprise a rinsing step between step a) and step b). In a further embodiment, the method may further comprise allowing hair treatment composition on hair for at least 5 minutes prior to step b. In yet a further embodiment, the method may provide the benefits of frizz reduction and conditioning after treatment last at least 5 washes. In a further embodiment, the method may provide the benefits of frizz reduction and conditioning after treatment last at least 10 washes. In a further embodiment, the method may provide the benefits of frizz reduction and conditioning after treatment last at least 20 washes. In an embodiment, the method may be used at a frequency of once a week. In a further embodiment, the method may be used at a frequency of once every two weeks. In yet a further embodiment, the method may be used once a month/every 30 days.

In an embodiment of the present invention, the composition may comprise additional silicone conditioning agents. The conditioning agent of the compositions of the present invention may be an insoluble silicone conditioning agent. The silicone conditioning agent droplets or particles may comprise volatile silicone, non-volatile silicones, or combinations thereof. In one aspect, non-volatile silicones conditioning agents are employed. If volatile silicones are present, it will typically be incidental to their use as a solvent or carrier for commercially available forms of non-volatile silicone materials ingredients, such as silicone gums and resins. The silicone conditioning agent droplets or particles may comprise a silicone fluid conditioning agent and may also comprise other ingredients, such as a silicone resin to improve silicone fluid deposition efficiency or enhance gloss of the hair.

The concentration of the silicone conditioning agent typically ranges from about 0.01% to about 10%, from about 0.1% to about 8%, from about 0.1% to about 5%, or even from about 0.2% to about 3%. Non-limiting examples of suitable silicone conditioning agents, and optional suspending agents for the silicone, are described in U.S. Reissue Pat. No. 34, 584, U.S. Pat. No. 5,104,646, and U.S. Pat. No. 5,106,609. The silicone conditioning agents for use in the compositions of the present invention typically have a viscosity, as measured at 25° C., from about 20 centistokes to about 2,000,000 centistokes ("cst"), from about 1,000 cst to about 1,800,000 cst, from about 50,000 cst to about 1,500,000 cst, or even from about 100,000 cst to about 1,500,000 cst.

a. Silicone Oils

Silicone fluids may include silicone oils, which are flowable silicone materials having a viscosity, as measured at 25° C., less than 1,000,000 cst, from about 5 cst to about 1,000,000 cst, or even from about 100 cst to about 600,000 cst. Suitable silicone oils for use in the compositions of the present invention include polyalkyl siloxanes, polyaryl siloxanes, polyalkylaryl siloxanes, polyether siloxane copolymers, and mixtures thereof. Other insoluble, non-volatile silicone fluids having hair conditioning properties may b. Amino and Cationic Silicones Compositions of the present invention may include an aminosilicone. Aminosilicones, as provided herein, are silicones containing at least one primary amine, secondary amine, tertiary amine, or a quaternary ammonium group.

In one embodiment, the amino silicone typically has a viscosity of from about 1,000 cst (centistokes) to about 1,000,000 cst, from about 10,000 to about 700,000 cst, from about 50,000 cst to about 500,000 cst, or even from about 100,000 cst to about 400,000 cst. This embodiment may also comprise a low viscosity fluid, such as, for example, those materials described below in Section F.(1). The viscosity of aminosilicones discussed herein is measured at 25° C.

In another embodiment, the amino silicone typically has a viscosity of from about 1,000 cst to about 100,000 cst, from about 2,000 cst to about 50,000 cst, from about 4,000 cst to about 40,000 cst, or even from about 6,000 cst to about 30,000 cst.

The aminosilicone typically is contained in the composition of the present invention at a level by weight of from about 0.05% to about 20%, from about 0.1% to about 10%, and or even from about 0.3% to about 5%.

c. Silicone Gums

Other silicone fluids suitable for use in the compositions of the present invention are the insoluble silicone gums. These gums are polyorganosiloxane materials having a viscosity, as measured at 25° C., of greater than or equal to 1,000,000 cst. Specific non-limiting examples of silicone gums for use in the compositions of the present invention include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

d. High Refractive Index Silicones

Other non-volatile, insoluble silicone fluid conditioning agents that are suitable for use in the compositions of the present invention are those known as "high refractive index silicones," having a refractive index of at least about 1.46, at least about 1.48, at least about 1.52, or even at least about 1.55. The refractive index of the polysiloxane fluid will generally be less than about 1.70, typically less than about 1.60. In this context, polysiloxane "fluid" includes oils as well as gums.

Silicone fluids suitable for use in the compositions of the present invention are disclosed in U.S. Pat. No. 2,826,551, U.S. Pat. No. 3,964,500, and U.S. Pat. No. 4,364,837.

e. Silicone Resins

Silicone resins may be included in the conditioning agent of the compositions of the present invention. These resins are highly cross-linked polymeric siloxane systems. The cross-linking is introduced through the incorporation of trifunctional and tetrafunctional silanes with monofunctional or difunctional, or both, silanes during manufacture of the silicone resin.

f. Modified Silicones or Silicone Copolymers

Other modified silicones or silicone copolymers are also useful herein. Examples of these include silicone-based quaternary ammonium compounds (Keenan quats) disclosed in U.S. Pat. Nos. 6,607,717 and 6,482,969; end-terminal quaternary siloxanes; silicone aminopolyalkyleneoxide block copolymers disclosed in U.S. Pat. Nos. 5,807,956 and 5,981,681; hydrophilic silicone emulsions disclosed in U.S. Pat. No. 6,207,782; and polymers made up of one or more crosslinked rake or comb silicone copolymer segments disclosed in U.S. Pat. No. 7,465,439. Additional modified silicones or silicone copolymers useful herein are described in US Patent Application Nos. 2007/0286837A1 and 2005/0048549A1.

In alternative embodiments of the present invention, the above-noted silicone-based quaternary ammonium compounds may be combined with the silicone polymers described in U.S. Pat. Nos. 7,041,767 and 7,217,777 and US Application number 2007/00. In a further embodiment of the present invention, the present invention may comprise fluorosilicone.

In an embodiment, the fluorosilicone may be hydrophobic and oleophobic and may also be insoluble but dispersible in the vehicle. There is essentially no restriction on the nature of the fluorosilicone. In one embodiment, the fluorosilicone will comprise a fluoro-substituted polyorganosiloxane. The fluorosilicone will typically comprise repeat units of the form $[Si(R_2)(R_3)O]$ wherein $R_2$ and/or $R_3$ are independently alkyl, aryl, or alkylaryl (e.g., benzyl) radicals, with at least one of $R_2$ and $R_3$ being substituted with one or more fluorine atoms. In an embodiment, at least one of $R_2$ or $R_3$ will be a $C_{1-30}$ alkyl group which comprises one or more fluorine atoms, and which preferably comprises, in an embodiment, a perfluoro segment, by which is meant a segment of the form $(CF2)_x$ where x is an integer from 1 to 29 and/or a trifluoromethyl group.

In an embodiment, a fluorosilicone has the following general structure of Formula:

where m is an integer from 1 to 5,000, in an embodiment from 1 to 200, in a further embodiment from 10 to 100, and in a further embodiment from 10 to 50; where n is an integer from 0 to 4,999, in an embodiment from 1 to 200, in a further embodiment from 10 to 100, and a further embodiment from 10 to 50; and wherein x is an integer from 0 to 12. One suitable fluorosilicone is Perfluorononyl Dimethicone sold under the trade names PECOSIL® FSL-150, FSL-300, FSH-150, FSH-300, FSU-150 and FSU-300 from Phoenix Chemical, Inc. which all have the chemical abstracts number CAS 259725-95-6.

In an embodiment of the present invention, without being bound by theory, it is believed that the silicone emulsion forms a thin film on hair with the amino function is attached to damage hair and the silicone portion imparting the silky feel and conditioning properties. In addition, it is believed that the silicone emulsion of the present invention further cross-links upon drying to form a more tenacious film. The film is resistant from washing for longer lasting benefits.

Silicones are known to be excellent hair conditioning agents. Their hydrophobic nature and their very low surface energy, enable them to easily spread on hair surfaces and imparting a soft feel. The partially cationic character that the aminofunctionality imparts to the siloxanes polymer of the current invention contributes to a strong interaction with the anionic and hydrophilic surface of oxidatively-damaged hair, improving the conditioning effectiveness. In addition, the high molecular weight of the deposited precrosslinked silicone agent, which further crosslinks upon deposition and drying, contributes to its low solubility/dispersibility in aqueous formulations. As a result, hair treated with such polysiloxanes is resistant toward washing, resulting in long lasting conditioning benefit over numerous shampoos.

In an embodiment of the present invention, essential oil and oil emulsion may also form oil film on hair surface to make hair softer and provide extra moisture barrier. Non-limiting examples may include Moringa oil and emulsions; Macademia oil and emulsions; Meadowfoam oil and emulsions; Argon oil and emulsions, mosa mint oil and emulsions and mixtures thereof.

Cationic Surfactant System

In an embodiment of the present invention, the composition may comprise a cationic surfactant system. The cationic surfactant system can be one cationic surfactant or a mixture of two or more cationic surfactants. Preferably, the cationic surfactant system is selected from: mono-long alkyl quaternized ammonium salt; a combination of mono-long alkyl quaternized ammonium salt and di-long alkyl quaternized ammonium salt; mono-long alkyl amidoamine salt; a combination of mono-long alkyl amidoamine salt and di-long alkyl quaternized ammonium salt, a combination of mono-long alkyl amindoamine salt and mono-long alkyl quaternized ammonium salt The cationic surfactant system is included in the composition at a level by weight of from about 0.1% to about 10%, preferably from about 0.5% to about 8%, more preferably from about 0.8% to about 5%, still more preferably from about 1.0% to about 4%.

Mono-Long Alkyl Quaternized Ammonium Salt

The monoalkyl quaternized ammonium salt cationic surfactants useful herein are those having one long alkyl chain which has from 12 to 30 carbon atoms, preferably from 16 to 24 carbon atoms, more preferably C18-22 alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the formula (I):

(I)

wherein one of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Preferably, one of $R^{75}$, $R^{76}$, $R^{77}$ and $R^{78}$ is selected from an alkyl group of from 12 to 30 carbon atoms, more preferably from 16 to 24 carbon atoms, still more preferably from 18 to 22 carbon atoms, even more preferably 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Non-limiting examples of such mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt.

Mono-Long Alkyl Amidoamine Salt

Mono-long alkyl amines are also suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al. These amines can also be used in combination with acids such as ℓ-glutamic acid, lactic acid, hydrochloric acid, malic acid, succinic acid, acetic acid, fumaric acid, tartaric acid, citric acid, ℓ-glutamic hydrochloride, maleic acid, and mixtures thereof; more preferably ℓ-glutamic acid, lactic acid, citric acid. The amines herein are preferably partially neutralized with any of the acids at a molar ratio of the amine to the acid of from about 1:0.3 to about 1:2, more preferably from about 1:0.4 to about 1:1.

Di-Long Alkyl Quaternized Ammonium Salt

Di-long alkyl quaternized ammonium salt is preferably combined with a mono-long alkyl quaternized ammonium salt or mono-long alkyl amidoamine salt. It is believed that such combination can provide easy-to-rinse feel, compared to single use of a monoalkyl quaternized ammonium salt or mono-long alkyl amidoamine salt. In such combination with a mono-long alkyl quaternized ammonium salt or mono-long alkyl amidoamine salt, the di-long alkyl quaternized ammonium salts are used at a level such that the wt % of the dialkyl quaternized ammonium salt in the cationic surfactant system is in the range of preferably from about 10% to about 50%, more preferably from about 30% to about 45%.

The dialkyl quaternized ammonium salt cationic surfactants useful herein are those having two long alkyl chains having 12-30 carbon atoms, preferably 16-24 carbon atoms, more preferably 18-22 carbon atoms. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Di-long alkyl quaternized ammonium salts useful herein are those having the formula (II):

(II)

wherein two of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Preferably, one of $R^{75}$, $R^{76}$, $R^{77}$ and $R^{78}$ is selected from an alkyl group of from 12 to 30 carbon atoms, more preferably from 16 to 24 carbon atoms, still more preferably from 18 to 22 carbon atoms, even more preferably 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Such dialkyl quaternized ammonium salt cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride. Such dialkyl quaternized ammonium salt cationic surfactants also include, for example, asymmetric dialkyl quaternized ammonium salt cationic surfactants.

High Melting Point Fatty Compound

In an embodiment of the present invention, the composition may comprise a high melting point fatty compound.

The high melting point fatty compound useful herein has a melting point of 25° C. or higher, and is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than 25° C. Such compounds of low melting point are not intended to be included in this section. Non-limiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are preferably used in the composition of the present invention. The fatty alcohols useful herein are those having from about 14 to about 30 carbon atoms, preferably from about 16 to about 22 carbon atoms. These fatty alcohols are saturated and can be straight or branched-chain alcohols. Preferred fatty alcohols include, for example, cetyl alcohol, stearyl alcohol, behenyl alcohol, and mixtures thereof.

High melting point fatty compounds of a single compound of high purity are preferred. Single compounds of pure fatty alcohols selected from the group of pure cetyl alcohol, stearyl alcohol, and behenyl alcohol are highly preferred. By "pure" herein, what is meant is that the compound has a purity of at least about 90%, preferably at least about 95%. These single compounds of high purity provide good rinsability from the hair when the consumer rinses off the composition.

The high melting point fatty compound is included in the composition at a level of from about 0.1% to about 20%, preferably from about 1% to about 15%, more preferably from about 1.5% to about 8% by weight of the composition, in view of providing improved conditioning benefits such as slippery feel during the application to wet hair, softness and moisturized feel on dry hair.

Gel Matrix

In an embodiment of the present invention, the composition of the present invention may comprise a gel matrix. The gel matrix comprises a cationic surfactant, a high melting point fatty compound, and an aqueous carrier.

The gel matrix is suitable for providing various conditioning benefits such as slippery feel during the application to wet hair and softness and moisturized feel on dry hair. In view of providing the above gel matrix, the cationic surfactant and the high melting point fatty compound are contained at a level such that the weight ratio of the cationic surfactant to the high melting point fatty compound is in the range of, preferably from about 1:1 to about 1:10, more preferably from about 1:1 to about 1:6.

Aqueous Carrier

The hair care composition of the present invention includes an aqueous carrier. Accordingly, the formulations of the present invention can be in the form of pourable liquids (under ambient conditions). Such compositions will therefore typically comprise an aqueous carrier, which is present at a level of from about 20 wt. % to about 95 wt. %, or even from about 60 wt. % to about 85 wt. %. The aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The aqueous carrier useful in the present invention includes water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

According to embodiments of the present invention, the hair care compositions may have a pH in the range from about 2 to about 10, at 25° C. In one embodiment, the hair care composition has a pH in the range from about 2 to about 6.

Solvents

According to an embodiment of the invention, the composition may include one or more solvents. In an embodiment, the composition may include one or more organic solvents. In a further embodiment of the invention, a solvent may include one or more of the following:

Hydrocarbons, branched or linear saturated or unsaturated (including aromatic) with total carbon atoms less than 15; Halogenated hydrocarbons, branched or linear saturated or unsaturated (including aromatic) with total carbon atoms less than 15; Alcohols, diols or polyols with total carbon atoms less than 8; Thiols or polythiols with total carbon atoms less than 8; Carboxylic acids with total carbon atoms less than 7; Carboxylic acid esters or carboxylic acid amides with total carbon atoms less than 8; Ketones or aldehydes with total carbon atoms less than 8; Ethers or polyethers with total carbon atoms less than 10; Amines or polyamines with total carbon atoms less than 8; Siloxane solvents; and Materials that contain a combination of the functional groups listed above.

In an embodiment of the present invention, a solvent may be a polyol, an alcohol having an aromatic functional group and combinations. In a further embodiment, a solvent may be butylene glycol, benzyl alcohol and combinations.

In an embodiment of the present invention, a solvent may be present in a range of about 0.1% to about 25%. In a further embodiment, a solvent may be present in a range of about 0.5% to about 20%. In yet a further embodiment, a solvent may be present in a range of about 1.0% to about 15%.

In an embodiment of the present invention, the solvent is volatile. In a further embodiment of the present invention, a solvent may have a boiling point of below or equal to 250° C. In a further embodiment, a solvent may have a boiling point of below or equal to 200° C.

Non-limiting examples of solvents may include dipropyleneglycol, propylene glycol, butylene glycol, 1,4-butanediol, 3-allyloxy-1,2-propanediol, dipropylene glycol n-butyl ether, 1,2-hexanediol, dimethyl isosorbide, ethanol, benzyl alcohol, 1,3-butanediol, 1,3-propanediol, 2,2'-thiodiethanol, and 1,6-hexanediol, or combinations thereof.

Rheology Modifiers

In one embodiment, the composition of the present invention may comprise a rheology modifier to increase the substantivity of the composition. Any suitable rheology modifier can be used. In an embodiment, the composition may comprise from about 0.05% to about 10% of a rheology modifier, in a further embodiment, from about 0.1% to about 10% of a rheology modifier, in yet a further embodiment, from about 0.5% to about 2% of a rheology modifier, in a further embodiment, from about 0.7% to about 2% of a rheology modifier, and in a further embodiment from about 1% to about 1.5% of a rheology modifier. In an embodiment, the rheology modifier may be a polyacrylamide thickener. In an embodiment, the rheology modifier may be a polymeric rheology modifier.

In one embodiment, the composition may comprise rheology modifiers that are homopolymers based on acrylic acid, methacrylic acid or other related derivatives, non-limiting examples include polyacrylate, polymethacrylate, polyethylacrylate, and polyacrylamide.

In another embodiment, the rheology modifiers may be alkali swellable and hydrophobically-modified alkali swellable acrylic copolymers or methacrylate copolymers non-limiting examples include acrylic acid/acrylonitrogens copolymer, acrylates/steareth-20 itaconate copolymer, acrylates/ceteth-20 itaconate copolymer, acrylates/aminoacrylates copolymer, acrylates/steareth-20 methacrylate copolymer, acrylates/beheneth-25 methacrylate copolymer, acrylates/steareth-20 methacrylate crosspolymer, acrylates/vinylneodecanoate crosspolymer, and acrylates/C10-C30 alkyl acrylate crosspolymer.

In a further embodiment, the rheology modifiers may be crosslinked acrylic polymers, a non-limiting example includes carbomers.

In a further embodiment, the rheology modifiers may be alginic acid based matertials, non-limiting examples include sodium alginate, and alginic acid propylene glycol esters.

In a further embodiment, the rheology modifier may be an associative polymeric thickeners, non-limiting examples include: Hydrophobically modified cellulose derivatives; Hydrophobically modified alkoxylated urethane polymers, nonlimiting example include PEG-150/decyl alcohol/SMDI copolymer, PEG-150/stearyl alcohol/SMDI copolymer, polyurethane-39; Hydrophobically modified, alkali swellable emulsions, non-limiting examples include hydrophobically modified polypolyacrylates, hydrophobically modified polyacrylic acids, and hydrophobically modified polyacrylamides; Hydrophobically modified polyethers wherein these materials may have a hydrophobe that can be selected from cetyl, stearyl, oleayl, and combinations thereof, and a hydrophilic portion of repeating ethylene oxide groups with repeat units from 10-300, in another embodiment from 30-200, in a further embodiment from 40-150. Non-limiting examples of this class include PEG-120-methylglucose dioleate, PEG-(40 or 60) sorbitan tetraoleate, PEG-150 pentaerythrityl tetrastearate, PEG-55 propylene glycol oleate, PEG-150 distearate.

In a further embodiment, the rheology modifier may be cellulose and derivatives, nonlimiting examples include Microcrystalline cellulose; Carboxymethylcelluloses; Hydroxyethylcellulose; Hydroxypropylcellulose; Hydroxypropylmethylcellulose; Methylcellulose; ethyl cellulose; nitro cellulose; cellulose sulfate; cellulose powder; Hydrophobically modified celluloses In an embodiment, the rheology modifier may be a guar and guar derivatives, non-limiting examples include hydroxypropyl guar, and hydroxypropyl guar hydroxypropyl trimonium chloride.

In an embodiment, the rheology modifier may be polyethylene oxide; polypropyne oxide; and POE-PPO copolymers.

In an embodiment, the rheology modifier may be polyvinylpyrrolidone, crosslinked polyvinylpyrrolidone and derivatives. In a further embodiment, the rheology modifier may be Polyvinyalcohol and derivatives.

In a further embodiment, the rheology modifier may be polyethyleneimine and derivatives.

In another embodiment, the rheology modifier may be silicas, non-limiting examples include fumed silica, precipitated silica, and silicone-surface treated silica.

In an embodiment, the rheology modifier may be water-swellable clays non-limiting examples include laponite, bentolite, montmorilonite, smectite, and hectonite.

In an embodiment, the rheology modifier may be gums non-limiting examples include xanthan gum, solagum Tara, guar gum, hydroxypropyl guar gum, Arabia gum, tragacanth, galactan, carob gum, karaya gum, and locust bean gum.

In a further embodiment, the rheology modifier may be, dibenzylidene sorbitol, karaggenan, pectin, agar, quince seed (Cydonia oblonga Mill), starch (from rice, corn, potato, wheat, etc), starch-derivatives (e.g. carboxymethyl starch, methylhydroxypropyl starch), algae extracts, dextran, succinoglucan, and pulleran, Non-limiting examples of rheology modifiers include acrylamide/ammonium acrylate copolymer (and) polyisobutene (and) polysorbate 20; acrylamide/sodium acryloyldimethyl taurate copolymer/isohexadecane/polysorbate 80; acrylates copolymer; acrylates/beheneth-25 methacrylate copolymer; acrylates/C10-C30 alkyl acrylate crosspolymer; acrylates/steareth-20 itaconate copolymer; ammonium polyacrylate/Isohexadecane/PEG-40 castor oil; C12-16 alkyl PEG-2 hydroxypropylhydroxyethyl ethylcellulose (HM-EHEC); carbomer; crosslinked polyvinylpyrrolidone (PVP); dibenzylidene sorbitol; hydroxyethyl ethylcellulose (EHEC); hydroxypropyl methylcellulose (HPMC); hydroxypropyl methylcellulose (HPMC); hydroxypropylcellulose (HPC); methylcellulose (MC); methylhydroxyethyl cellulose (MEHEC); PEG-150/decyl alcohol/SMDI copolymer; PEG-150/stearyl alcohol/SMDI copolymer; polyacrylamide/C13-14 isoparaffin/laureth-7; polyacrylate 13/polyisobutene/polysorbate 20; polyacrylate crosspolymer-6; polyamide-3; polyquaternium-37 (and) hydrogenated polydecene (and) trideceth-6; polyurethane-39; sodium acrylate/acryloyldimethyltaurate/dimethylacrylamide; crosspolymer (and) isohexadecane (and) polysorbate 60; sodium polyacrylate. Exemplary commercially-available rheology modifiers include ACULYN™ 28, Klucel M CS, Klucel H CS, Klucel G CS, SYLVACLEAR AF1900V, SYLVACLEAR PA1200V, Benecel E10M, Benecel K35M, Optasense RMC70, ACULYN™ 33, ACULYN™ 46, ACULYN™ 22, ACULYN™ 44, Carbopol Ultrez 20, Carbopol Ultrez 21, Carbopol Ultrez 10, Carbopol Ulterez 30, Carbopol 1342, Sepigel™ 305, Simulgel™ 600, Sepimax Zen, and combinations thereof.

According to yet another embodiment, the hair care composition may further include one or more additional hair growth stimulating agents, such as those disclosed in U.S. Patent Application Publication No. 2010/0120871. Accordingly, non-limiting examples of additional hair growth stimulating agents include indole compounds, xanthine compounds, vitamin $B_3$ compounds, panthenol compounds, and derivatives thereof.

Optional Ingredients

In accordance with embodiments of the present invention, the composition may further comprise one or more optional ingredients, including benefit agents. Suitable benefit agents include, but are not limited to conditioning agents, silicone emulsions, anti-dandruff actives, non-limiting examples include pyridinethione salts, such as zinc pyrithione, azoles, and selenium sulfide, gel networks, chelating agents, and natural oils such as sun flower oil or castor oil. Additional suitable optional ingredients include but are not limited to perfumes, perfume microcapsules, colorants, particles, antimicrobials, foam busters, anti-static agents, rheology modifiers and thickeners, suspension materials and structurants, pH adjusting agents and buffers, preservatives, pearlescent agents, solvents, diluents, anti-oxidants, vitamins and combinations thereof.

Such optional ingredients should be physically and chemically compatible with the components of the composition, and should not otherwise unduly impair product stability, aesthetics, or performance. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein.

Anti-Frizz Test Methods and Performance:

a) Application method: Naturally frizzy low lift hair switches (4 g in weight, 6 inches in length) are washed with a clarifying shampoo (conventional clarifying shampoo commercially available) and air dried. Three hair switches are treated with each leave on treatment (LOT) composition at 0.1 g/g dosage, massaged for 30 seconds and blow dried, then flat ironed using BaBylissPRO Nano Titanium 1 flat iron with a heat setting of 40. Treated hair switches are kept in a dry box with CaSO$_4$ desiccant (at approximate 22% Relative Humidity (RH)) until transferred to a 15% RH/90 F constant humidity constant temperature (CHCT) room to equilibrate overnight. This prevented the hair from being exposed to moisture in the ambient lab air. After the overnight (>8 hours) equilibration, the hair switches are then moved to a 80 F/80% RH CTCH room and images are taken immediately every 5 minutes or every hour until 3 hours or longer.

b) Shampoo wash method: The treated hair are washed with clarifying shampoo for 1 to 5 washes, each wash uses 0.1 g shampoo/1 g hair which is massaged into the hair for 30 seconds and rinsed thoroughly. The hair switches are then blow dried and flat ironed using the same conditions described above. They are placed in the frizz test as described above.

c) Anti-frizz performance assessment method: The images of the hair switches from the frizz test above are used to evaluate the anti-frizz performance of each treatment. This is done by measuring the width of hair switch images before and after exposure to humidity. Lower final width and change of width means better anti-frizz performance. It is demonstrated in experiment 1 that hair treated with compositions corresponding to the present invention (Ex. 1 and Ex. 2 in example table) has significantly smaller final width and change of width vs. hair treated with composition containing comparative silicone emulsion (Comp 1 in example table using HC303 commercially available from Wacker).

Table 1 are hair widths obtained from different treatments, after exposure to 80 F/80% RH for 7 days.

TABLE 1

Final width of hair switches after exposed to humidity for different treatment compositions.

| LOT Treatment | Final Width (cm) |
|---|---|
| Water | 13.1 |
| Ex. 1 | 5.9 |

TABLE 1-continued

Final width of hair switches after exposed to humidity for different treatment compositions.

| LOT Treatment | Final Width (cm) |
|---|---|
| Ex. 2 | 6.9 |
| Comp. 1 | 12.7 |

Durable Deposition, Conditioning and Anti-Frizz Performance:

1. Silicone deposition durability towards subsequent shampoo washes measured by Cryo-SEM-EDS (Scanning Electron Microscopy: Energy Dispersive Spectroscopy): Hair switches treated with LOT compositions and shampooed 5 times as described above are submitted for Cryo SEM-EDS measurements. 10 hair strands from each source are taped with conductive double sided tape onto the SEM substrate. Quick drying carbon paint is applied to the ends of the hairs and edges of the carbon tape. The samples are plunge frozen in liquid N2, then transferred to the Gatan Alto cryo-prep chamber. The specimens are sublimated at $-95°$ C. for 30 minutes, then coated with Au/Pd for approximately 65-100 seconds. Imaging is performed on the Hitachi S-4700 at 3 KV and 20 µA. EDS is performed with a Bruker 30 mm$^2$ SDD detector. Data is summarized in Table 2.

2. From the Cryo-EDS spectra it is clear that even after 5 clarifying shampoo washes, hair treated with the present invention there is still a significant amount of silicone left on hair, where the water treated control and the commercial LOT (contains non-cross-linked silicone gum and dimethicone fluid) treated hair had essentially zero or nearly zero amount silicone left.

TABLE 2

Cryo-EDS signal strength of silicone on hair treated with different compositions

| Treatment | Signal strength (proportional to silicone concentration) after 5× shampoo washes |
|---|---|
| Treated with water (baseline) | 0.14 cps/eV |
| Treated with commercial LOT (containing non-cross-linked silicone) | 0.21 cps/eV |
| Treated with Ex. 1 | 2.4 cps/eV |

Silicone deposition durability towards subsequent shampoo washes measured by silicone extraction: Hair switches are treated as described previously by Application Method except that one set of hair switches are left air dry without blow drying or flat ironing with Ex. 3 and then washed with clarifying shampoo. This treatment/washing process is repeated for 20 times. Then, silicone is extracted from the treated hair and quantified (Initial silicone content A). After this step, the treated hair is further washed by clarifying shampoo for a total of 10 times. At the end of 1, 5 and 10 washes, hair samples are extracted (by adding 0.1-0.2 grams of hair cut in 1 cm long into vials containing 2 ml extraction solvent (50/50 MIBK/Toluene). Silicone deposition can be measured by Inductively Coupled Plasma Optical Emission Spectroscopy (ICP-OES). Silicone is extracted from hair samples with 50:50 toluene: methylisobutyl ketone and the extracted samples are compared to ICP calibration standards of known silicone concentration. The vials are placed into a foam rack and put onto a multi-vortexer. The vials are pulsed at 2 seconds on/1 second off, 2500 power for 30 minutes. Initial silicone content A is determined from hair switches after the 20 times treatment/washing process. The silicone contents remaining on hair are measured after 1, 5 and 10 subsequent shampoo washes and are calculated as a percentage of initial silicone content A. A high percentage remaining after the shampoo cycles indicates high durability of the silicone treatment. The results presented below in Table 3 correspond to the average value from 3 hair switches.

TABLE 3

| % silicone remaining after x shampoo washes | End of 20 LOT/SH cycles (baseline) | Remaining silicone on hair after 1 shampoo wash as the percentage of the initial silicone content | Remaining silicone on hair after 5 shampoo washes as the percentage of initial silicone content | Remaining silicone on hair after 10 shampoo washes as the percentage of initial silicone content |
|---|---|---|---|---|
| Flat Iron after each LOT/SH cycles | 100% | 90% | 96% | 81% |
| Air Dry after each LOT/SH cycle | 100% | 114%* | 88% | 72% |

*greater than 100% due to method variability

3. Long lasting anti-frizz benefit: Hair switches are treated with different compositions and shampooed according to the Anti-frizz test methods and performance described above. Table 4 summarizes the hair width of different treatments measured after exposure to 80 F/80% RH for 7 days before and after one to five shampoo washes. It is can be seen that the hair switch treated with present invention had significant smaller change in width than treated with water and Comp 1 with HC303 (commercially available from Wacker) after the humidity exposure. Smaller change in hair width corresponds to better anti-frizz performance.

TABLE 4

| Treatment | Wash Cycles | Initial | Final (width cm) | Change |
|---|---|---|---|---|
| Water | 0 | 5.8 | 12.7 | 6.9 |
| Ex 1 | 0 | 2.3 | 3.7 | 1.5 |
| Comp.1 | 0 | 4.5 | 12.7 | 8.2 |
| Water | 1 | 4.0 | 6.5 | 2.5 |
| Ex 1 | 1 | 3.8 | 4.6 | 0.7 |
| Comp 1 (HC303) | 1 | 4.9 | 11.6 | 6.7 |
| Water | 3 | 5.0 | 8.1 | 3.1 |
| Ex 1 | 3 | 4.1 | 5.9 | 1.8 |
| Water | 5 | 3.9 | 7.4 | 3.5 |
| Ex 1 | 5 | 3.0 | 5.3 | 2.2 |

4. Long lasting conditioning benefits: Long lasting conditioning benefits are measured by Friction Reduction on Wet Hair (Instron Double Comb or IDC) as well as on dry hair (Inter fiber method, IFM).

Hair preparation method for IDC and IFM measurements: Hair is prewashed 2 lathers containing 0.05 gram of non-conditioning shampoo per gram of hair. A quantity of 0.05 gram of leave-on product per gram of hair is applied in zig zag dots and spread thoroughly milking the hair switch for 30 seconds without rinsing-off. The hair switch is combed using a fine toothed comb 5 times to further distribute product. The hair is tested using the wet IDC method.

For the IFM measurements, the treated hair switches are hanged to dry in a room at 73° F. and 45% RH for at least 18 hours. The hair is tested using the dry IFM method in a 73° F./45% Relative Humidity (RH) Lab.

Wet Instron Double Comb method (Wet IDC) and IFM determine the force necessary to pass a comb through a switch of hair in the wet and dry states respectively. They can be used to evaluate the conditioning effectiveness of shampoo and conditioner products. The hair switches used weigh 4 grams and contain "special quality" Caucasian hair fibers of 8 inches in length. The switches are treated with the products as described above. An Inston 5542 or 5543 Tensile Tester with an attachment for combing hair switches and an Instron 2530-437 50N tension/compression Load cell is used. The switches are mounted on the instrument and the force required to comb the switches measured. The extension speed is 15 mm/sec, the extension length is 240 mm and the reading time interval is 0.5 sec. In all experiments at least 5 readings are performed on each switch and at least 3 switches are used for each treatment. Low combing force corresponds to more effective conditioning.

Figure 1:
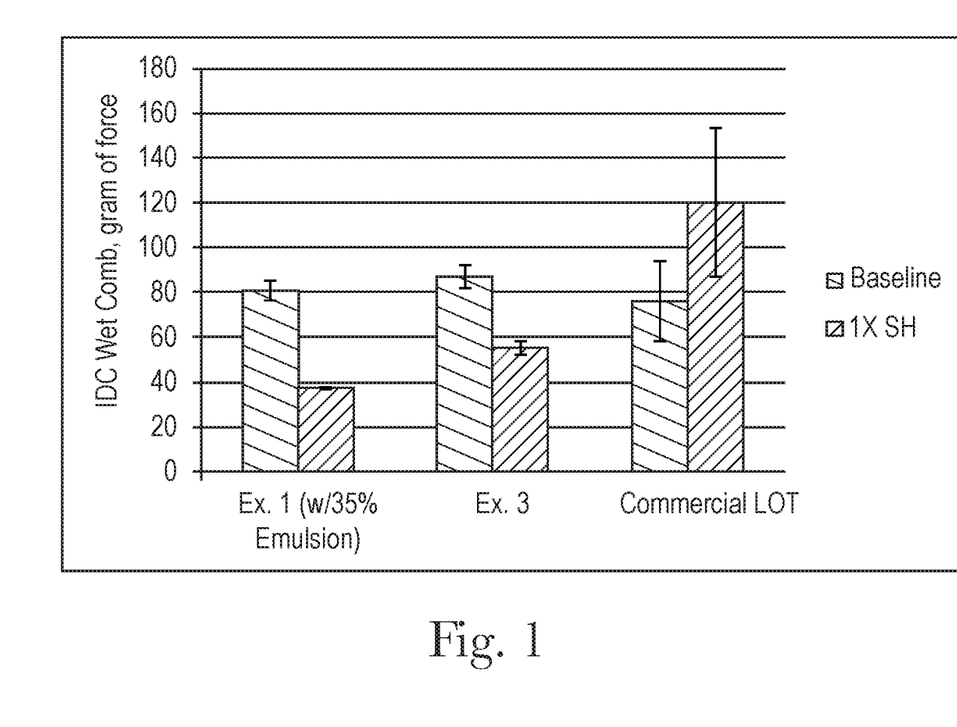
FIG. 1 is a graph demonstrating comparison of hair switches treated with various leave-on-treatment compositions before and after shampoo washing wherein friction reduction on wet hair is evaluated via a hair friction force measurement (Index IDC).
Figure 2:
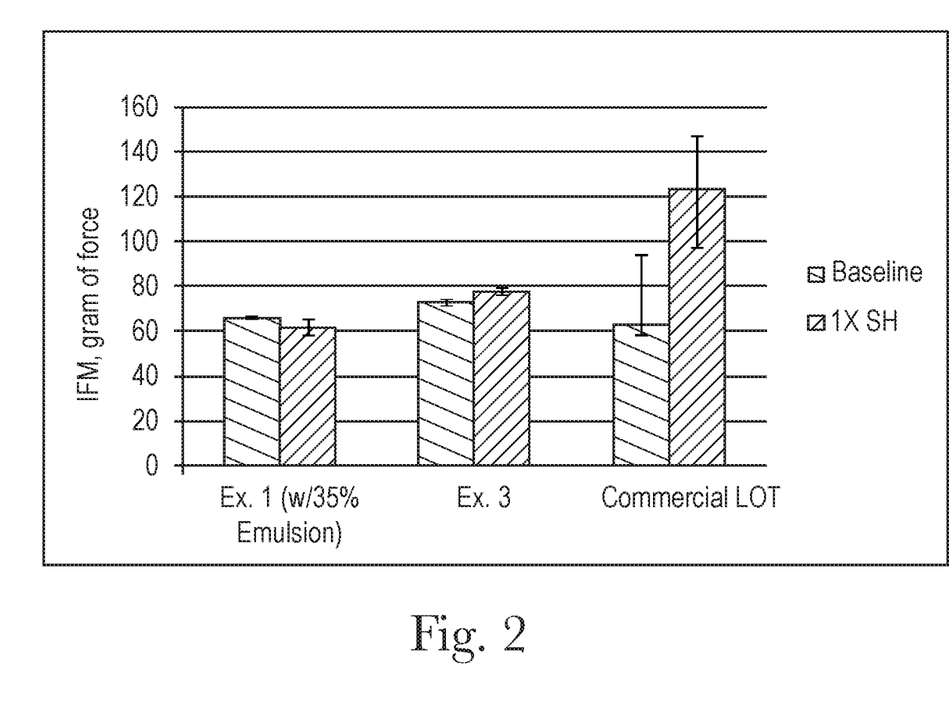
FIG. 2 is a graph demonstrating comparison of hair switches treated with various leave-on-treatment compositions before and after shampoo washing wherein dry conditioning performance is evaluated via a hair friction force measurement (Index IFM).

Long lasting conditioning benefits are measured after treating hair switches with the composition and after shampooing, following the shampoo method as described above. As the data shows in FIG. 1 and FIG. 2, hair treated with the composition of the present invention (baseline; before shampoo washing) has good conditioning benefits shown by low friction in IDC wet comb and IFM (dry) compared to a commercial LOT. Further, these results demonstrate that after 1 shampoo wash (1× SH), while the friction of hair treated with the commercial LOT increases significantly (indication of loss of conditioning benefits), the friction of hair treated with the compositions of the present invention does not increase significantly after the shampoo cycle. This demonstrates that the method of treating the hair with the present invention composition provides durable conditioning benefits towards subsequent washing.

Impact of emulsion droplet size to anti-frizz performance: Anti-frizz evaluations are performed on hair using the same treatment protocol as described above. Emulsions of two different average particle diameters are used to determine the effect of this parameter on the treatment effectiveness. The first treatment emulsion (Wacker Belsil ADM 8301E) has an average diameter size of less than 50 nm, whereas the second treatment emulsion (Wacker 6300E) has an average particle diameter size of less than 250 nm.

In Table 5, a comparison of hair switches treated with emulsion 8301E vs. hair switches treated with emulsion 6300E demonstrates that the smaller particle size emulsion outperforms the larger particle size emulsion significantly (smaller change is better). This effect may be due to better and more even filming formation on hair shaft.

TABLE 5

| Treatment | Initial Width (cm) | Final Width (cm) | Change (cm) |
|---|---|---|---|
| <250 nm | 5.1 | 9.0 | 4.4 |
| <50 nm | 4.4 | 7.0 | 2.6 |

EXAMPLES

1. LOT Spray with Silicone Emulsion.

| Components | Ex 1 | Ex 2 | Ex 3 | Ex 4 | Ex 5 | Ex 6 | Ex 7 | Comp 1 |
|---|---|---|---|---|---|---|---|---|
| 20% silicone emulsion[1] | 20 | 10 | 20 | 20 | 20 | 10 | 10 | — |
| 20% oil emulsion[3] | — | — | 30 | 20 | 10 | 20 | 30 | — |
| Other Silicone | — | — | — | — | — | — | — | 4%[2] |
| Behenyltrimethyl ammonium chloride[4] | — | — | — | 0.5 | 0.5 | 0.5 | 0.5 | — |
| Benzyl alcohol | 0.4 | 0.4 | 0.4 | 0.4 | 0.4 | 0.4 | 0.4 | 0.4 |
| Methylchloroisothiazonlinone/ ethylisothiazonlinone | .005 | .005 | .005 | .005 | .005 | .005 | .005 | 0.005 |
| Perfume | 0.6 | 0.6 | 0.6 | 0.6 | 0.6 | 0.6 | 0.6 | 0.6 |
| Water | q.s. | q.s. | q.s. | q.s. | q.s. | q.s. | q.s. | q.s. |

[1]Wacker Belsil ADM 8301E;
[2]Wacker HC303;
[3]Moringa oil emulsion comprising 20% moringa oil, 6% ethylene glycol, 1.7% Tween 20, 0.77% sorbitan ester (SPAN 60 from Croda; Moringa oil available from FLORATECH
[4]Behenyltrimethylammonium chloride, Genamin KDMP, from Clariant

2. LOT with Silicone, Silicone Emulsion and Oil Emulsion and Gel Matrix

| Components | Ex 8 | Ex 9 | Ex 10 | Ex 11 | Ex 12 | Ex 13 | Ex 14 |
|---|---|---|---|---|---|---|---|
| Silicone[1] | 4.0 | 4.0 | 4.0 | — | — | — | 2.0 |
| 20% Silicone emulsion[2] | — | — | — | 20 | 20 | 20 | — |
| 20% oil emulsion[3] | — | 20 | 10 | — | 20 | 10 | 20 |
| SAPDMA[4] | 0.60 | 0.60 | 0.60 | 0.60 | 0.60 | 0.60 | 0.60 |
| Cetyl Alcohol[5] | 1.3 | 1.3 | 1.3 | 1.3 | 1.3 | 1.3 | 1.3 |
| Hydroxyethyl Cellulose[6] | 0.45 | 0.45 | 0.45 | 0.45 | 0.45 | 0.45 | 0.45 |
| Quaternium-18 | 0.45 | 0.45 | 0.45 | 0.45 | 0.45 | 0.45 | 0.45 |
| Benzyl Alcohol | 0.40 | 0.40 | 0.40 | 0.40 | 0.40 | 0.40 | 0.40 |
| Polyox WSR N-10 PEG 2M[7] | 0.30 | 0.30 | 0.30 | 0.30 | 0.30 | 0.30 | 0.30 |
| Methylparaben, NF | 0.20 | 0.20 | 0.20 | 0.20 | 0.20 | 0.20 | 0.20 |
| Oleyl Alcohol | 0.15 | 0.15 | 0.15 | 0.15 | 0.15 | 0.15 | 0.15 |
| Glyceryl Stearate | 0.15 | 0.15 | 0.15 | 0.15 | 0.15 | 0.15 | 0.15 |
| Propylparaben, NF | 0.15 | 0.15 | 0.15 | 0.15 | 0.15 | 0.15 | 0.15 |
| Panthenol Solution | 0.09 | 0.09 | 0.09 | 0.09 | 0.09 | 0.09 | 0.09 |
| Panthenyl Ethyl ether | 0.05 | 0.05 | 0.05 | 0.05 | 0.05 | 0.05 | 0.05 |
| Water | q.s. | q.s. | q.s. | q.s. | q.s. | q.s. | q.s. |

[1]Dimethicone from Momentive
[2]Wacker Belsil ADM 8301E
[3]Moringa oil emulsion comprising 20% moringa oil, 6% ethylene glycol, 1.7% Tween 20, 0.77% sorbitan ester (SPAN 60 from Croda; Moringa oil available from FLORATECH
[4]Stearamidopropyldimethylamine is supplied by Inolex as Lexamine S-13
[5]Cetyl alcohol supplied by P&G
[6]Hydroxyethylcellulose; supplied by Ashland as Natrosol 250 GR
[7]Nonionic poly(ethylene oxide) polymer 2M is supplied by Dow as Poyox WSR N-10

3. LOT with Silicone Emulsion, Oil Emulsion and Thickener

| Components | Ex 15 | Ex 16 | Ex 17 | Ex 18 | Ex 19 | Ex 20 | Ex 21 |
|---|---|---|---|---|---|---|---|
| 20% silicone emulsion[1] | 20 | 20 | 20 | 20 | 20 | 10 | 10 |
| 20% oil emulsion[2] | — | 20 | 30 | 20 | 10 | 20 | 30 |
| Behenyl trimethyl ammonium chloride[3] | — | — | 0.5 | 0.5 | 0.5 | 0.5 | 0.5 |
| Benzyl alcohol | 0.4 | 0.4 | 0.4 | 0.4 | 0.4 | 0.4 | 0.4 |
| Methylchloroisothiazonlinone/ ethylisothiazonlinone | .005 | .005 | .005 | .005 | .005 | .005 | .005 |
| Sepigel 305[4] | 1.0 | 1.0 | 1.0 | 1.0 | 1.0 | 1.0 | 1.0 |
| Perfume | 0.6 | 0.6 | 0.6 | 0.6 | 0.6 | 0.6 | 0.6 |
| Water | q.s. | q.s. | q.s. | q.s. | q.s. | q.s. | q.s. |

[1]Wacker Belsil ADM 8301E
[2]Moringa oil emulsion comprising 20% moringa oil, 6% ethylene glycol, 1.7% Tween 20, 0.77% sorbitan ester (SPAN 60 from Croda; Moringa oil available from FLORATECH
[3]Behenyltrimethylammonium chloride, Genamin KDMP, from Clariant
[4]Sepigel ™ 305 from Seppic

4. Shampoo Formulas

| Components | Ex. 22 | Ex. 23 | Ex. 24 | Ex. 25 | Ex. 26 | Ex. 27 | Ex. 28 | Ex. 29 | Ex. 30 |
|---|---|---|---|---|---|---|---|---|---|
| Water | q.s. | q.s. | q.s. | q.s. | q.s. | q.s. | q.s. | q.s. | q.s. |
| Sodium Laureth Sulfate[1] | 13.0 | 12.0 | 13.0 | 10.5 | 10.5 | 10.5 | 10.5 | 12.0 | 12.0 |
| Sodium Lauryl Sulfate[2] | 1.5 | 1.5 | 1.5 | 1.5 | 1.5 | 1.5 | 1.5 | 1.5 | 1.5 |
| CMEA[3] | — | — | 0.8 | — | — | — | 0.8 | — | — |
| Cocoamidopropyl Betaine[4] | 1.7 | 1.7 | 1.0 | 1.0 | 1.0 | 1.0 | 1.0 | 1.7 | 1.7 |
| Guar Hydroxypropyl Trimonium Chloride[5] | 0.325 | 0.3 | — | — | — | — | — | 0.30 | — |
| Polyquaternium-10[6] | 0.075 | — | — | — | — | — | — | — | 0.30 |
| Polyquaternium-6[7] | 0.075 | — | 0.1 | — | — | — | — | — | — |
| 20% Silicone Emulsion[8] | 5.0 | 10.0 | 100 | 10.0 | 10.0 | 7.5 | 7.5 | 7.5 | 7.5 |
| Glycerin[9] | 0.5 | 0.5 | — | — | — | — | — | — | — |
| EGDS[10] | — | — | 1.5 | — | — | — | 1.5 | — | — |
| Trihydroxystearin[11] | 0.1 | 0.1 | — | 0.1 | 0.1 | 0.1 | — | 0.1 | 0.1 |
| Fragrance, preservatives, viscosity adjustment | Up to 3% | Up to 3% | Up to 3% | Up to 3% | Up to 3% | Up to 3% | Up to 3% | Up to 3% | Up to 3% |
| pH adjustment | | | | pH = 5.5-6.5 | | | | | |

[1]Sodium Laureth-1 Sulfate, from Stepan
[2]Sodium Lauryl Sulfate, from P&G
[3]Ninol Comf, from Stepan
[4]Amphosol HCA-B, from Stepan
[5]NHance-3196, from ASI
[6]Ucare Polymer KG-30M, from The Dow Chemical Company
[7]Mirapol 100, from Rhodia Inc
[8]Wacker Belsil ADM 8301E
[9]Superol V GlycerinUSP, from P&G
[10]EGDS pure, from Evonik
[11]Thixcin R from Elementis 5. The following examples illustrate embodiments of the present invention wherein the silicone polymer is emulsified.

| Components | Ex. 31 | Ex. 32 | Ex. 33 | Ex. 34 | Ex. 35 | Ex. 36 | Ex. 37 | Ex. 38 | Ex. 39 |
|---|---|---|---|---|---|---|---|---|---|
| Water | q.s. | q.s. | q.s. | q.s. | q.s. | q.s. | q.s. | q.s. | q.s. |
| Sodium Laureth Sulfate[1] | 13.0 | 12.0 | 10.5 | 10.5 | 10.5 | 10.5 | 10.5 | 12.0 | 12.0 |
| Sodium Lauryl Sulfate[2] | 1.5 | 1.5 | 1.5 | 1.5 | 1.5 | 1.5 | 1.5 | 1.5 | 1.5 |
| CMEA[3] | — | — | 0.8 | — | — | — | 0.8 | — | — |
| Cocoamidopropyl Betaine[4] | 1.7 | 1.7 | 1.0 | 1.0 | 1.0 | 1.0 | 1.0 | 1.7 | 1.7 |
| Guar Hydroxypropyl Trimonium Chloride[5] | 0.325 | 0.3 | — | — | — | — | — | 0.30 | — |
| Polyquaternium-10[6] | 0.075 | — | — | — | — | — | — | — | 0.30 |
| Polyquaternium-6[7] | 0.075 | — | 0.25 | — | — | — | — | — | — |
| Silicone Emulsion[8] | 5.0 | 5.0 | 5.0 | 10 | 10 | 5.0 | 2.5 | 2.5 | 2.5 |
| Oil[9] | | | | | | 5.0 | 5.0 | 2.5 | 2.5 |
| Glycerine[10] | 0.5 | 0.5 | — | — | — | — | — | — | — |
| EGDS[11] | — | — | 1.5 | — | — | — | 1.5 | — | — |
| Trihydroxystearin[12] | 0.1 | 0.1 | — | 0.1 | 0.1 | 0.1 | — | 0.1 | 0.1 |

| Components | Ex. 31 | Ex. 32 | Ex. 33 | Ex. 34 | Ex. 35 | Ex. 36 | Ex. 37 | Ex. 38 | Ex. 39 |
|---|---|---|---|---|---|---|---|---|---|
| Fragrance, preservatives, viscosity adjustment | Up to 3% | Up to 3% | Up to 3% | Up to 3% | Up to 3% | Up to 3% | Up to 3% | Up to 3% | Up to 3% |

[1]Sodium Laureth-1 Sulfate, from Stepan
[2]Sodium Lauryl Sulfate, from P&G
[3]Ninol Comf, from Stepan
[4]Amphosol HCA-B, from Stepan
[5]NHance-3196, from ASI
[6]Ucare Polymer KG-30M, from The Dow Chemical Company
[7]Mirapol 100, from Rhodia Inc.
[8]Wacker Belsil ADM 8301E
[9]Moringa oil emulsion comprising 20% moringa oil, 6% ethylene glycol, 1.7% Tween 20, 0.77% sorbitan ester (SPAN 60 from Croda; Moringa oil available from FLORATECH
[10]Superol V Glycerine USP, from P&G
[11]EGDS pure, from Evonik
[12]Thixcin R from Elementis 6. The following examples illustrate embodiments of the present invention in rinse off conditioner with the silicone emulsion.

| Ingredient | Parts% Ex. 40 | Parts% Ex. 41 | Parts% Ex. 42 | Parts% Ex. 43 |
|---|---|---|---|---|
| Dow Corning AP-6087 | 2.5 | 2.0 | 1.5 | 1.0 |
| Silicone emulsion[1] | 2.5 | 5.0 | 7.5 | 10 |
| BTMS[2] | 4.36 | 4.36 | 4.36 | 4.36 |
| Stearyl alcohol | 4.32 | 4.32 | 4.32 | 4.32 |
| Cetyl alcohol | 1.73 | 1.73 | 1.73 | 1.73 |
| Perfume | 0.5 | 0.5 | 0.5 | 0.5 |
| Benzyl alcohol | 0.4 | 0.4 | 0.4 | 0.4 |
| Disodium EDTA | 0.127 | 0.127 | 0.127 | 0.127 |
| panthenol | 0.03 | 0.03 | 0.03 | 0.03 |
| Panthenyl Ethyl ether | 0.03 | 0.03 | 0.03 | 0.03 |
| Water | | | | |

[1]Wacker ADM Belsil 8301E
[2]Behenyltrimethylammonium methylsulfate

The exemplified compositions can be prepared by conventional formulation and mixing techniques. It will be appreciated that other modifications of the hair care composition within the skill of those in the hair care formulation art can be undertaken without departing from the spirit and scope of this invention. All parts, percentages, and ratios herein are by weight unless otherwise specified. Some components may come from suppliers as dilute solutions. The amount stated reflects the weight percent of the active material, unless otherwise specified.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A method of reduction of frizz and improving hair conditioning wherein a hair treatment composition comprising a silicone emulsion with droplets having an average diameter of less than about 50 nanometers (nm) in an carrier wherein the silicone emulsion comprises a crosslinked organopolysiloxane made from various reactive compounds, wherein each compound is comprised of one or more units represented by the following general formula:

where
R$^1$ is morpholinomethyl having the structure:

R$^2$ is
—(CH$_2$)$_3$—NH—(CH$_2$)$_2$NH$_2$
—(CH$_2$)$_3$—NH$_2$
R$^3$ is methyl
R$^4$ is hydrogen, methyl, ethyl or propyl
n is 0, 1, or 2
m is 0, 1, or 2
p is 0, 1, or 2
q is 0, 1, 2 or 3
n+m+p+q is less than or equal to 3
and wherein the crosslinked organopolysiloxane comprises on average at least one radical
R$^1$ per molecule wherein the hair treatment composition has a pH in the range from about 2 to about 6 and wherein the method comprises the following steps:
   a) applying the hair treatment composition to hair by spraying or spreading;
   b) allowing hair to dry by air or heat.
2. A method according to claim 1 wherein it further comprises a rinsing step between step a) and step b).

3. A method according to claim 1 wherein it further comprises allowing hair treatment composition on hair for at least about 5 minutes prior to step b.

4. A method according to claim 1 wherein the benefits of frizz reduction and conditioning after treatment last at least about 5 washes.

5. A method according to claim 1 wherein the benefits of frizz reduction and conditioning after treatment last at least about 10 washes.

6. A method according to claim 1 wherein the benefits of frizz reduction and conditioning after treatment last at least about 20 washes.

7. A method according to claim 1 wherein the method is used at a frequency of about once a week.

8. A method according to claim 1 wherein the method is used at a frequency of about once every two weeks.

9. A method according to claim 1 wherein the method is used about once a month/every about 30 days.

10. A method according to claim 1 wherein at least about 50% silicone remains on the hair after treatment.

11. A method according to claim 1 wherein the hair treatment composition further comprises an additional conditioner agent.

12. A method according to claim 11 wherein the hair treatment composition further comprises a gel matrix.

13. A method according to claim 11 wherein the hair treatment composition further comprises oils, essential oils, oil emulsions and mixtures thereof.

14. A method according to claim 13 wherein the hair treatment composition further comprises moringa oil and emulsions, macademia oil and emulsions, meadowfoam oil and emulsions, argon oil and emulsions, mosa mint oil and emulsions and mixtures thereof.

* * * * *